United States Patent [19]

Ogawa et al.

[11] Patent Number: 5,830,913
[45] Date of Patent: Nov. 3, 1998

[54] METHOD FOR PREVENTING OR TREATING DRY EYE OR DISEASE CAUSED THEREFROM

[75] Inventors: Takahiro Ogawa, Nishinomiya; Noriko Watanabe, Suita; Yasushi Okumura, Amagasaki, all of Japan

[73] Assignees: Tanabe Seiyaku Co., Ltd.; Senju Pharmaceutical Co., Ltd., both of Osaka, Japan

[21] Appl. No.: 747,647

[22] Filed: Nov. 13, 1996

[30] Foreign Application Priority Data

Nov. 15, 1995 [JP] Japan ................................. 7-322364

[51] Int. Cl.$^6$ ..................................................... A61K 31/19
[52] U.S. Cl. ............................................................. 514/569
[58] Field of Search ............................................. 514/569

[56] References Cited

U.S. PATENT DOCUMENTS 4,529,602  7/1985  Wada et al. .............................. 514/569

FOREIGN PATENT DOCUMENTS

0078152A1  5/1983  European Pat. Off. .
WO9513087  5/1995  WIPO .

OTHER PUBLICATIONS

Onoda et al., Japan. J. Pharmacol., vol. 52, No. 4, pp. 631–638 (1990).

*Primary Examiner*—Raymond Henley, III
*Attorney, Agent, or Firm*—Birch, Stewart, Kolasch & Birch, LLP

[57] ABSTRACT

There is disclosed a pharmaceutical composition for preventing or treating dry eye or a disease caused therefrom which comprises as an active ingredient an effective amount of sulfodehydroabietic acid or a pharmacologically acceptable salt thereof. There are also disclosed a method and device for preventing or treating dry eye or a disease caused therefrom.

4 Claims, 7 Drawing Sheets

FIG. 13

METHOD FOR PREVENTING OR TREATING DRY EYE OR DISEASE CAUSED THEREFROM

FIELD OF THE INVENTION

The present invention relates to a pharmaceutical composition, method and device for preventing or treating dry eye or a disease caused therefrom.

BACKGROUND OF THE INVENTION

"Dry eye" has hitherto been referred to as xerophthalmia, hypolacrimation, keratoconjunctivitis sicca and the like. However, since the conception of dry eye is expansive or wide and the cause of dry eye is unknown in many cases, it is considered that dry eye is not a single disease but a disease of the ocular surface, including disease which should be called dry eye syndrome. Now, dry eye is defined as a state where the quantity and quality of the tears is abnormal regardless of the keratoconjunctival lesion (Masakazu YAMADA et al., Nippon Ganka Kiyo, 43, 1289–1293 (1992)). According to this definition, the category of dry eye includes diseases such as hypolacrimation, tear deficiency, xerophthalmia, Sjögren's syndrome, keratoconjunctivitis sicca, Stevens-Johnson syndrome, ocular pemphigoid, blepharitis marginal, lid-closure failure, sensory nerve paralysis and the like. In addition, the category of dry eye includes allergic conjunctivitis-associated dry eye, post-viral conjunctivitis dry eye and post-cataract surgery dry eye.

In addition, due to increase in contact lens wearers, increase in time spent in artificially air-conditioned environments and increase in an opportunity to gaze at a VDT (video (visual) display terminal) screen because of the widespread use of televisions, computers and word processors, the factors which promote dry eye have been recently increased and contact lens wearing-associated dry eye and VDT operation-associated dry eye are increasing.

Further, when one is affected with dry eye, a tear lacks any one of an oily layer, an aqueous layer and a mucin layer in many cases, which causes keratoconjunctival lesion. In particular, when a tear lacks the mucin layer, corneal lesion is severe, which easily causes not only corneal epithelial lesion and corneal epithelial erosion derived from corneal epithelial cell lesion but also corneal ulcer (for example, an ulcer of the corneal stromal layer) and ocular infectious disease. In some cases, corneal transplantation becomes necessary. These are diseases caused by dry eye.

At present, as a method for treating dry eye, there is no causal treatment and symptomatic treatment is merely carried out. As a symptomatic treatment, application to the eye of an artificial tear containing a viscoelastic substance such as methylcellulose, chondroitin sulfate and hyaluronic acid as a substitute for mucin is mainly carried out. However, since these substances are physically and physiologically different from mucin, the therapeutic effects are limited. Therefore, there is now no satisfying method for treating dry eye and no pharmaceutical composition for treating the same.

OBJECTS OF THE INVENTION

One object of the present invention is to provide an excellent pharmaceutical composition for preventing or treating dry eye or a disease caused therefrom.

Another object of the present invention is to provide an excellent method for preventing or treating dry eye or a disease caused therefrom.

Another object of the present invention is to provide an excellent device for preventing or treating dry eye or a disease caused therefrom.

These objects as well as other objects and advantages of the present invention will become apparent to those skilled in the art from the following description with reference to the accompanying drawings.

SUMMARY OF THE INVENTION

In order to find a pharmaceutical composition, method and device for preventing or treating dry eye or a disease caused therefrom, the present inventors studied hard as discussed below.

As described above, when one is affected with dry eye, in particular, when the mucin layer is deficient, corneal lesion is severe. Mucin adheres to corneal epithelial cells and imparts hydrophilic characteristics to the corneal surface so as to stably keep a tear on the ocular surface. In addition, since mucin has a large saccharide content, it functions to keep the corneal and conjunctival surface wet or moist and capture and remove extraneous matter and bacteria. Therefore, it is thought that the environment more similar to an intact tear of the living body can be made on the ocular surface by applying mucin into a tear of dry eye patients.

In addition, it is known that mucin is produced from conjunctival goblet cells and the function of conjunctival goblet cells of dry eye patients is decreased as compared with that of healthy subjects (Nelson J D, et al., Arch. Ophthalmol., 102, 1049–1051 (1984)). Therefore, it is thought that dry eye can be treated and further prevented by applying into a tear of dry eye patients a drug which improves the function of goblet cells or promotes the mucopolysaccharide producing function of goblet cells.

The present inventors searched a variety of compounds from these points of view. As a result, the present inventors found that sulfodehydroabietic acid or a pharmacologically acceptable salt thereof (hereinafter sometimes referred to as "present compound") described in Japanese laid open publication 58-77814, Japanese laid open publication 63-165361 and Japanese laid open publication 2-167258, in particular, sulfodehydroabietic acid monosodium salt which is the representative compound thereof, unexpectedly has the activity to promote the mucopolysaccharide producing function of goblet cells and inhibits keratinizing keratoconjunctival lesion based on decrease in the above function, which resulted in completion of the present invention.

The above Japanese laid open publications describe that the present compound is useful as an anti-ulcer agent but do not describe that the present compound inhibits keratinizing keratoconjunctival lesion based on decrease in the function of goblet cells. The present inventors were the first to discover such inhibition.

The present invention provides a pharmaceutical composition for preventing or treating dry eye or a disease caused therefrom which comprises as an active ingredient an effective amount of a compound represented by the formula (I):

sulfodehydroabietic acid (chemical name; 1,4a-dimethyl-1-carboxy-6-sulfo-7-isopropyl-1,2,3,4,4a,9,10,10a-octahydrophenanthrene) or a pharmacologically acceptable salt thereof and a pharmaceutically acceptable carrier suitable for topical administration.

The present invention also provide a method for preventing or treating dry eye or a disease caused therefrom which comprises applying to an eye of a patient a pharmaceutical composition comprising as an active ingredient an effective amount of a compound represented by the formula (I):

or a pharmacologically acceptable salt thereof and a pharmaceutically acceptable carrier.

The present invention further provides a device for preventing or treating dry eye or a disease therefrom, which comprises:

a container;

a pharmaceutical composition comprising as an active ingredient an effective amount of a compound represented by the formula (I):

or a pharmacologically acceptable salt thereof; and a pharmaceutically acceptable carrier contained within said container; and instructions for using the device for preventing or treating dry eye or a disease caused therefrom, wherein said instructions are physically attached to said container or packaged together with said container.

In the present invention, an ophthalmic solution (hereinafter sometimes referred to as eyedrops) containing sulfodehydroabietic acid monosodium salt as an active ingredient is preferable. The concentration of the salt is preferably 0.05 to 1.0 (w/v) %.

The pharmaceutical composition of the present invention is useful for preventing or treating dry eye such as hypolacrimation, tear deficiency, xerophthalmia, Sjögren's syndrome, keratoconjunctivitis sicca, Stevens-Johnson syndrome, ocular pemphigoid, blepharitis marginal, lid-closure failure and sensory nerve paralysis, allergic conjunctivitis-associated dry eye, post-viral conjunctivitis dry eye, post-cataract surgery dry eye, VDT operation-associated dry eye and contact lens wearing-associated dry eye as well as diseases caused by dry eye such as keratoconjunctival epithelial lesion, corneal epithelial erosion, corneal ulcer and ocular infectious disease.

DETAILED DESCRIPTION OF THE INVENTION

Sulfodehydroabietic acid is the compound represented by the formula (I). The compound represented by the formula (I) or a pharmacologically acceptable salt thereof is used in an effective amount as an active ingredient in the pharmaceutical composition of the present invention for preventing or treating dry eye or a disease caused therefrom. The compound represented by the formula (I) is known and can be prepared according to a method described in Japanese laid open publication 58-77814, Japanese laid open publication 63-165361 and Japanese laid open publication 2-167258 or a similar method.

Examples of a pharmacologically acceptable salt of sulfodehydroabietic acid represented by the formula (I) include salts with an alkaline metal such as sodium, lithium, potassium and the like, an alkaline earth metal such as magnesium, calcium and the like, aluminum and the like. Among these, the preferable salt is a sodium salt of sulfodehydroabietic acid and the most preferable salt is a monosodium salt of sulfodehydroabietic acid. A monosodium salt of sulfodehydroabietic acid is the preferred salt due to the fact that it is less hygroscopic and more stable than a disodium salt of the same (Japanese laid open publication 63-165361). A pharmacologically acceptable salt of sulfodehydroabietic acid can also exist as a hydrate. Examples of the hydrate of sulfodehydroabietic acid monosodium salt include pentahydrate (that is, sulfodehydroabietic acid monosodium salt pentahydrate) and the like. Sulfodehydroabietic acid monosodium salt pentahydrate is a compound with the general name sodium ecabet (sometimes referred to as "present compound A" in this specification).

The pharmaceutical composition of the present invention, referring to a compound useful in preventing or treating dry eye or a disease caused therefrom, has the activity to promote the mucopolysaccharide producing function of goblet cells which produce mucin. This delays the progression of keratinizing keratoconjunctival lesion as apparent from Test Examples below. Therefore, the pharmaceutical composition of the present invention is useful for preventing or treating dry eye or a disease caused therefrom.

As used herein, "dry eye" is a wide concept which is intended to include diseases such as hypolacrimation, tear deficiency, xerophthalmia, Sjögren's syndrome, keratoconjunctivitis sicca, Stevens-Johnson syndrome, ocular pemphigoid, blepharitis marginal, lid-closure failure and sensory nerve paralysis, allergic conjunctivitis-associated dry eye, post-viral conjunctivitis dry eye, post-cataract surgery dry eye, VDT operation-associated dry eye and contact lens wearing-associated dry eye as well as diseases caused by dry eye such as keratoconjunctival epithelial lesion, corneal epithelial sores, corneal ulcers (such as ulcers of corneal stromal layer) and ocular infectious disease.

When the present compound is used in a pharmaceutical composition for preventing or treating dry eye or a disease caused therefrom, it is usually mixed with a pharmacologically acceptable carrier, excipient, diluent or the like which is known itself. The present compound is prepared into parenteral preparations such as ophthalmic solution, ophthalmic ointments, injections or oral preparations such as tablets, capsules and granules. The preferable dosage is an ophthalmic solution.

When the pharmaceutical composition of the present invention for preventing or treating dry eye or a disease caused therefrom is used as an ophthalmic solution, it is provided in any dosage form which is used for ophthalmic solution, for example, an aqueous eye drop such as aqueous ophthalmic solution, aqueous suspended ophthalmic solution, viscous ophthalmic solution and solubilized ophthalmic solution, or a non-aqueous ophthalmic solution such as non-aqueous ophthalmic solution and non-aqueous suspended ophthalmic solution. Among these, the aqueous ophthalmic solution is preferable.

When the pharmaceutical composition of the present invention for preventing or treating dry eye or a disease caused therefrom is prepared into an aqueous ophthalmic solution, various additives normally used in the aqueous ophthalmic solution are conveniently contained therein as long as the object of the present invention is not adversely affected. Examples of such the additives include buffers, isotonizing agents, preservatives, solubilizers (stabilizers), pH adjusting agents, thickeners and chelating agents.

The buffers may be selected from but not limited by the group comprising a phosphate buffer, a borate buffer, a citrate buffer, a tartrate buffer, an acetate buffer (for example, sodium acetate) and an amino acid.

The isotonizing agents may be selected from but not limited by the group comprising sugars such as sorbitol, glucose and mannitol, polyhydric alcohols such as glycerin, polyethylene glycol and polypropylene glycol, and salts such as sodium chloride.

The preservatives may be selected from but not limited by the group comprising benzalkonium chloride, benzethonium chloride, alkyl paraoxybenzoates such as methyl paraoxybenzoate and ethyl paraoxybenzoate, benzyl alcohol, phenethyl alcohol, sorbic acid and salts thereof, thimerosal and chlorobutanol.

The solubilizers (stabilizers) may be selected from but not limited by the group comprising cyclodextrin and derivatives thereof, water-soluble polymers such as poly (vinylpyrrolidone), and surfactants such as polysorbate 80 (trade name: Tween 80).

The pH adjusting agents may be selected from but not limited by the group comprising hydrochloric acid, acetic acid, phosphoric acid, sodium hydroxide, potassium hydroxide and ammonium hydroxide.

The thickeners may be selected from but not limited by the group comprising hydroxyethylcellulose, hydroxypropylcellulose, methylcellulose, hydroxypropylmethylcellulose and carboxymethylcellulose and salts thereof.

The chelating agents may be selected from but not limited by the group comprising sodium edetate, sodium citrate and sodium condensed phosphate.

When the pharmaceutical composition of the present invention for preventing or treating dry eye or a disease caused therefrom is prepared into an ophthalmic ointment, a base compound must be present. The base of the ophthalmic ointment may be selected from but not limited by the group comprising purified lanolin, vaseline, plastibase, liquid paraffin and polyethylene glycol.

In addition to ophthalmic solution and ophthalmic ointment preparations, the pharmaceutical composition of the present invention for preventing or treating dry eye or a disease caused therefrom can be formulated into parenteral preparations such as injections, and oral preparations such as tablet, capsule and granule.

The pharmaceutical composition of the present invention may be placed within a first sterile container. The sterile container may be placed in a second container, such as a box. The first sterile container or the second container may have instructions thereon for preventing or treating dry eye or a disease caused therefrom. Alternatively, or in addition, the instructions may be placed inside the second container. The instructions may be printed on a label on either of the two containers.

The sterile container may be a bottle having an eye dropper in the cap or lid thereof, a squeeze tube with an ointment or eye drop solution therein, a squeeze bottle with an eye drop solution therein, a bottle, a jar, and a travel-sized packet.

The label may be an external stick-on label, an internal label, and an attached set of directions clearly labelled, a package insert and the like.

The pharmaceutical composition of the present invention for preventing or treating dry eye or a disease caused therefrom can be administered to a mammal (such as a human being, rabbit, dog, cat, cattle, horse, monkey and the like). A dose of the pharmaceutical composition of the present invention depends upon the mode of administration, the symptom(s) present, and the age and weight of a patient. For example, when the pharmaceutical composition of the present invention is used as an ophthalmic solution for an adult dry eye patient, it is desirable that an aqueous solution eye drop, containing as an active ingredient the present compound, for example, the present compound A in an amount of approximately 0.001 to 2.5 (w/v) %, preferably 0.05 to 1.0 (w/v) %, is administered at a dose of one to a few drops, once to 8 times per day. The dose also depends upon the symptom(s) present.

When the pharmaceutical composition of the present invention is used as an ocular ointment, it is desirable that an ocular ointment, containing as an active ingredient the present compound A in an amount of approximately 0.001 to 2.5 (w/w) %, preferably 0.05 to 1.0 (w/w) %, is administered once to 4 times per day. The dose also depends upon the symptom(s) present.

In addition, one or more other agents for preventing or treating dry eye or a disease caused therefrom, such as an artificial tear containing a viscoelastic substance such as methylcellulose, chondroitin sulfate and hyaluronic acid can be added to the pharmaceutical composition of the present invention.

The following Examples and Test Example illustrate the present invention in detail but are not to be interpreted as limiting to the scope thereof.

EXAMPLE 1

Ophthalmic Solution

An ophthalmic solution was prepared based on the following formulation according to a conventional method.

| | |
|---|---|
| Present compound A | 0.5 g |
| Sodium acetate | 0.1 g |
| Concentrated glycerin | 2.6 g |
| Methyl parahydoxybenzoate | 0.026 g |
| Propyl parahydoxybenzoate | 0.014 g |
| Chlorobutanol | 0.3 g |
| Polyvinylpyrrolidone | 1.0 g |
| Sterile purified water | ad. 100 ml |
| | (pH 5.0) |

EXAMPLE 2

Ophthalmic Solution

An ophthalmic solution was prepared based on the following formulation according to a conventional method.

| | |
|---|---|
| Present compound A | 0.05 g |
| Sodium acetate | 0.1 g |
| Concentrated glycerin | 2.6 g |
| Methyl parahydoxybenzoate | 0.026 g |
| Propyl parahydoxybenzoate | 0.014 g |
| Chlorobutanol | 0.3 g |
| Polyvinylpyrrolidone | 1.0 g |
| Sterile purified water | ad. 100 ml |
| | (pH 5.0) |

EXAMPLE 3

Ophthalmic Solution

An ophthalmic solution was prepared based on the following formulation according to a conventional method.

| | |
|---|---|
| Present compound A | 0.5 g |
| Sodium acetate | 0.1 g |
| Concentrated glycerin | 2.6 g |
| Methyl parahydoxybenzoate | 0.026 g |
| Propyl parahydoxybenzoate | 0.014 g |
| Chlorobutanol | 0.3 g |
| Sterile purified water | ad. 100 ml |
| | (pH 5.0) |

EXAMPLE 4

Ophthalmic Solution

An ophthalmic solution was prepared based on the following formulation according to a conventional method.

| | |
|---|---|
| Present compound A | 0.5 g |
| Disodium hydrogen phosphate | 0.1 g |

-continued

| | |
|---|---|
| dodecahydrate | |
| Concentrated glycerin | 2.6 g |
| Polysorbate 80 | 0.1 g |
| Benzalkonium chloride | 0.005 g |
| Sterile purified water | ad. 100 ml |
| | (pH 7.0) |

EXAMPLE 5

Ophthalmic Solution

An ophthalmic solution was prepared based on the following formulation according to a conventional method.

| | |
|---|---|
| Present compound A | 0.05 g |
| Disodium hydrogen phosphate dodecahydrate | 0.1 g |
| Sodium chloride | 0.9 g |
| Polysorbate 80 | 0.1 g |
| Benzalkonium chloride | 0.005 g |
| Sterile purified water | ad. 100 ml |
| | (pH 7.0) |

EXAMPLE 6

Ophthalmic Solution

An ophthalmic solution was prepared based on the following formulation according to a conventional method.

| | |
|---|---|
| Present compound A | 0.5 g |
| Disodium hydrogen phosphate dodecahydrate | 0.1 g |
| Sodium chloride | 0.9 g |
| Polysorbate 80 | 0.1 g |
| Sodium hydroxide | q.s. |
| Sterile purified water | ad. 100 ml |
| | (pH 7.0) |

TEST EXAMPLE

The activity of the present compound A in delaying the progress of keratinizing keratoconjunctival lesion was studied using a vitamin A deficient rat showing the symptoms of keratinizing keratoconjunctival lesion which was established from the hypofunction of goblet cells.

Test Drug

An ophthalmic solution obtained in Example 6 (0.5% present compound A eyedrops) was used. As a control, a physiological saline solution was used.

Animal to be Used

Three-week-old SD male rats which had been bred with a vitamin A deficient feed for about 180 days were used. As a normal group, three-week-old SD male rats which had been bred with a normal feed for about 180 days was used.

Experimental Procedures

Administration of a test drug was initiated at a point when corneal keratinization was recognized on nasal paracentral cornea of the rats bred with a vitamin A deficient feed. The test drug was applied to one eye in an amount of 5 µl, 8 times per day, for 20 days. Rats which received the test drug were subjected to the following experiments (1), (2) and (3).

(1) Observation with Slitlamp

A keratinized part of corneal epithelium was stained with 0.1% sodium fluorescein and the corneal keratinization was observed using a slitlamp for 21 days after the first instillation of test drugs. Evaluation was carried out by scoring according to the criteria shown in Table 1.

TABLE 1

| Score | Criteria |
|---|---|
| 0 | No staining is recognized on cornea. |
| 1 | Scattered punctate staining is recognized on cornea. |
| 2 | Punctate staining is recognized partially as a group on paracentral cornea. |
| 3 | Disciform staining area is recognized on nasal paracentral cornea. |
| 4 | Disciform staining area is recognized on a wide region of paracentral cornea. |
| 5 | Densely disciform staining is recognized on a wide region of paracentral cornea |

(2) Observation of Goblet Cells by Impression cytology

A MF Millipore membrane filter (membrane filter manufactured by NIPPON MILLIPORE LIMITED, aperture: 0.22 µm) was pressed against nasal bulbar conjunctiva and cells were collected on the filter's side using impression cytology. The collected cells were double-stained with Alcian Blue-PAS and the morphology of goblet cells on the conjunctival epithelial surface was observed and photographed with a photomicroscope (VANBOX manufactured by Olympus Kogakukogyo).

(3) Observation of Inferior Fornix Conjunctivae Goblet Cells with Scanning Electron Microscope (SEM)

Twenty-one days after the first instillation of test drug, the eyeball was isolated together with the palpebral conjunctiva attached thereto. An SEM specimen was prepared according to a conventional method and inferior fornix conjunctive goblet cells were observed and photographed with a scanning electron microscope.

Results of Test (1) Results of Observation with Slitlamp

The keratinized state of cornea of each vitamin A deficient rat was scored and evaluated according to the criteria shown in Table 1, the results of which are shown in Table 2. Values in Table 2 show the scores of the keratinized state of cornea. Respective values represent the scores of two samples (No. 1 and No. 2) in a group where an eye drop containing 0.5% present compound A was applied (hereinafter referred to as "0.5%" present compound A applied group) and two samples (No. 3 and No. 4) in a physiological saline solution applied group.

TABLE 2

| | 0.5% present compound A applied group | | Physiological saline solution applied group | |
|---|---|---|---|---|
| Days | No. 1 | No. 2 | No. 3 | No. 4 |
| 1 | 3.0 | 3.0 | 3.0 | 3.0 |
| 2 | 3.0 | 2.0 | 3.0 | 3.5 |
| 4 | 3.0 | 2.5 | 3.0 | 4.5 |
| 8 | 2.5 | 2.0 | 4.0 | 5.0 |
| 12 | 2.0 | 2.5 | 5.0 | 5.0 |
| 16 | 2.5 | 3.0 | 5.5 | 5.0 |
| 21 | 3.0 | 3.0 | 5.0 | 5.0 |

As apparent from the results shown in Table 2, it was seen that a 0.5% present compound A applied group inhibits the progress of corneal keratinization as compared with a physiological saline solution applied group.

Figure 1:
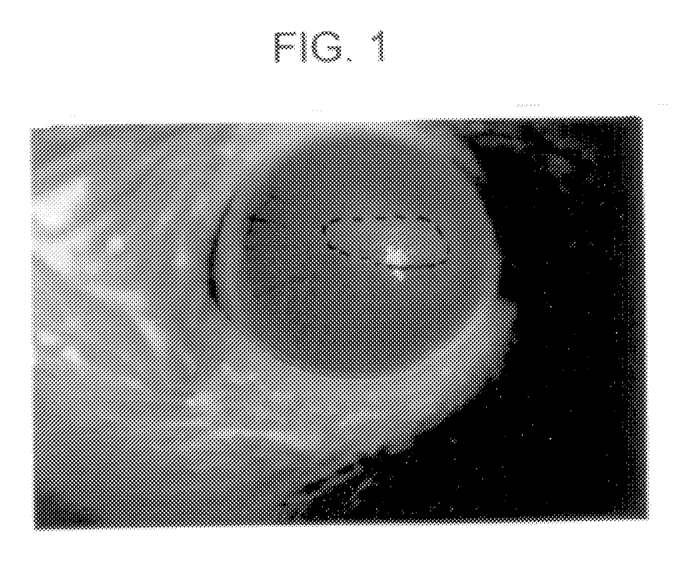
FIG. 1 is a photograph which shows the corneal keratinized state of the eye of a vitamin A deficient rat (No. 1) before application to the eye of an ophthalmic solution obtained in Example 6 below (hereinafter referred to as "0.5% present compound A eyedrops") and before application to the eye of a physiological saline solution. The eye was photographed using a slitlamp in accordance with Test Example, experimental procedure (1) below.
Figure 2:
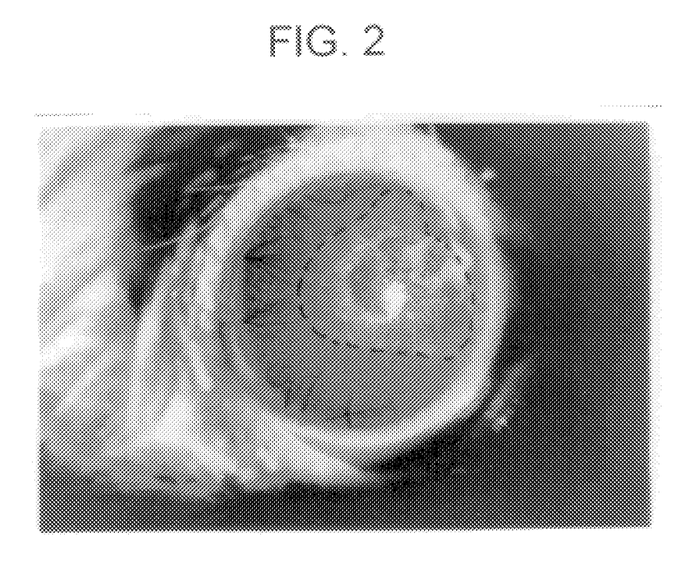
FIG. 2 is a photograph which shows the corneal keratinized state of the eye of a vitamin A deficient rat (No. 4) which had received application of a physiological saline solution 8 times per day for 20 days. The eye was photographed using a slitlamp in accordance with Test Example, experimental procedure (1) below.
Figure 3:
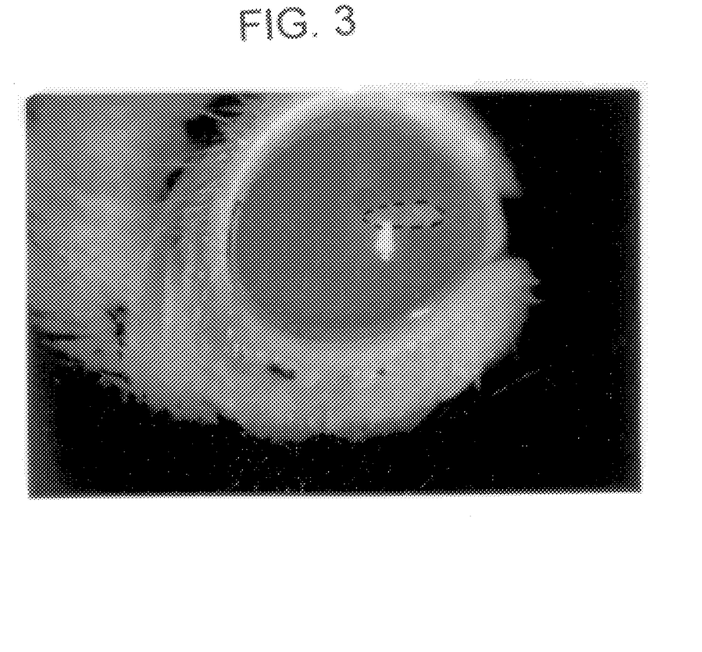
FIG. 3 is a photograph of the corneal keratinized state of the eye of a vitamin A deficient rat (No. 2) which had received application of a 0.5% present compound A eyedrops 8 times per day for 20 days. The eye was photographed using a slitlamp in accordance with Test Example, experimental procedure (1) below.

In addition, the results of the observation of the corneal keratinized state with a slitlamp are shown in FIGS. 1 to 3.

FIG. 1 is a photograph showing the corneal keratinized state of the eye of a vitamin A deficient rat (No. 1) before application of a 0.5% present compound A eyedrops or a physiological saline solution. The photograph was taken with a slitlamp. Corneal staining with fluorescein within the dashed line shows the corneal keratinization. The whitely sparkling part of paracentral cornea results from halation of the slitlamp.

FIG. 2 is a photograph showing the corneal keratinized state of the eye of a vitamin A deficient rat (No. 4) which had received application of a physiological saline solution 8 times per day for 20 days. The photograph was taken with a slitlamp. Corneal staining with fluorescein within the dashed line shows the corneal keratinization. The keratinized area is wider than before application of a physiological saline solution. The whitely sparkling part of paracentral cornea results from halation of the slitlamp.

FIG. 3 is a photograph showing the corneal keratinized state of the eye of a vitamin A deficient rat (No. 2) which had received application of a 0.5% present compound A eyedrops 8 times per day for 20 days. The photograph was taken with a slitlamp. Corneal staining with fluorescein within the dashed line shows the corneal keratinization. The keratinized area is approximately equal or decreased in size in comparison with the area before application. The whitely sparkling part of paracentral cornea results from halation of a slitlamp.

As apparent from FIGS. 1 and 2, keratinizing corneal lesion in a physiological saline solution applied group gradually worsened from the time of instillation (see FIG. 1), and progressed into a wider region (see FIG. 2). On the other hand, in a 0.5% present compound A applied group, the symptoms at 20 days after application was almost the same as that before application and, thus, it was observed that the progress of keratinizing lesion was inhibited (see FIG. 3).

(2) Results of Observation of Bulbar Conjunctival Goblet Cells by Impression Cytology The results of observation of bulbar conjunctival goblet cells by impression cytology are shown in FIGS. 4 to 7.

Figure 4:
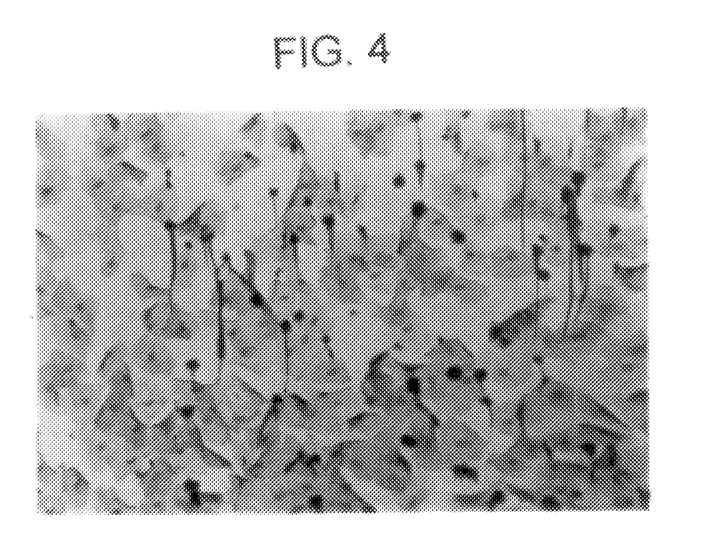
FIG. 4 is a light microscopic photograph of nasal bulbar conjunctival cells of a normal rat which were collected by impression cytology, stained by an Alcian Blue-PAS method and photographed with a photomicroscope in accordance with Test Example, experimental procedure (2) below.

FIG. 4 is a light microscopic photograph of nasal bulbar conjunctival cells from the eye of a normal rat. The cells were collected by impression cytology, stained by an Alcian Blue-PAS method and photographed with a photomicroscope. The stained area (reddish purple) indicates mucopolysaccharide. Goblet cells are not observed.

Figure 5:
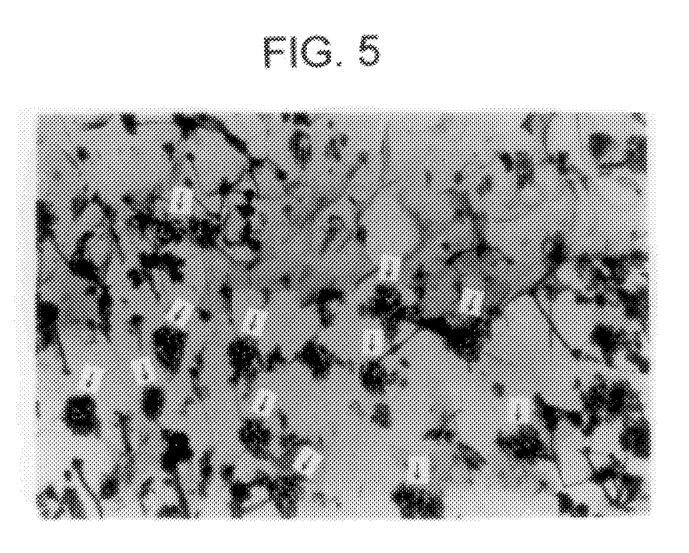
FIG. 5 is a light microscopic photograph of nasal bulbar conjunctival cells of a vitamin A deficient rat which were collected by impression cytology, stained by an Alcian Blue-PAS method and photographed with a photomicroscope in accordance with Test Example, experimental procedure (2) below.

FIG. 5 is a light microscopic photograph of nasal bulbar conjunctival cells from the eye of a vitamin A deficient rat. The cells were collected by impression cytology, stained by an Alcian Blue-PAS method and photographed with a photomicroscope. The arrows point at goblet cells and the stained area (reddish purple) indicates mucopolysaccharide. Mucopolysaccharide is also present in goblet cells.

Figure 6:
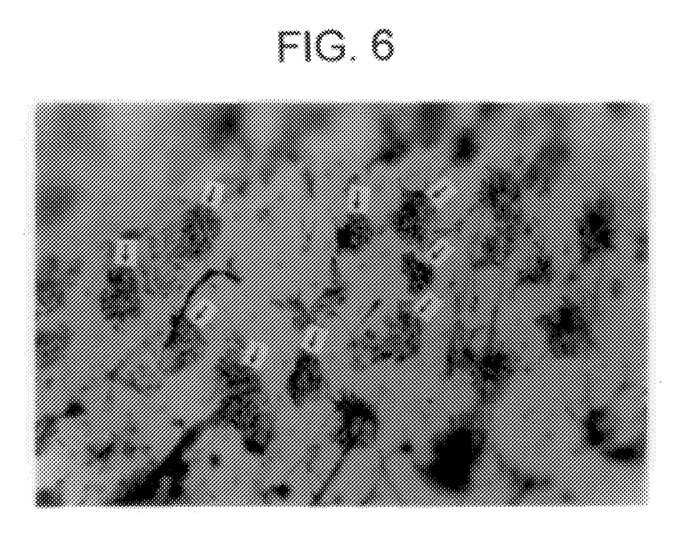
FIG. 6 is a light microscopic photograph of nasal bulbar conjunctival cells from the eye of a vitamin A deficient rat to which was applied a physiological saline solution 8 times per day for 20 days. The cells were collected by impression cytology, stained by an Alcian Blue-PAS method and photographed with a photomicroscope in accordance with Test Example, experimental procedure (2) below.

FIG. 6 is a light microscopic photograph of nasal bulbar conjunctival cells from the eye of a vitamin A deficient rat to which was applied a physiological saline solution 8 times per day for 20 days. The cells were collected by impression cytology, stained by an Alcian Blue-PAS method and photographed with a photomicroscope. The arrows point at goblet cells and the stained area (reddish purple) indicates mucopolysaccharide. Mucopolysaccharide is present within goblet cells in a small amount.

Figure 7:
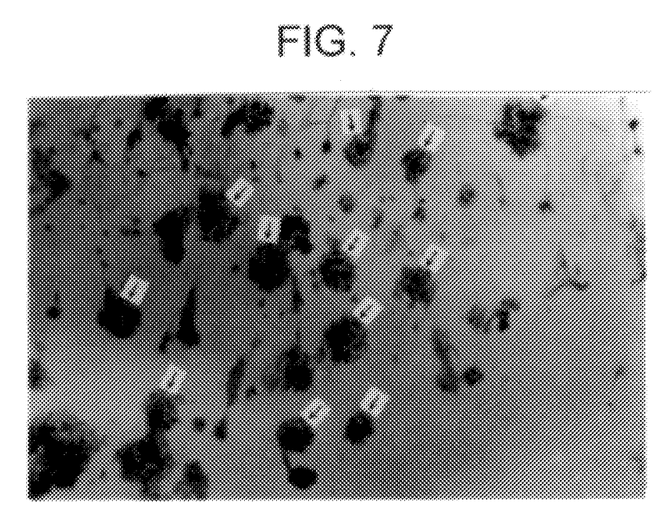
FIG. 7 is a light microscopic photograph of nasal bulbar conjunctival cells from the eye of a vitamin A deficient rat to which was applied a 0.5% present compound A eyedrops 8 times per day for 20 days. The cells were collected by impression cytology, stained by an Alcian Blue-PAS method and photographed with a photomicroscope in accordance with Test Example, experimental procedure (2) below.

FIG. 7 is a light microscopic photograph of the nasal bulbar conjunctival cells from the eye of a vitamin A deficient rat to which was applied a 0.5% present compound A eyedrops 8 times per day for 20 days. The cells were collected by impression cytology, stained with an Alcian Blue-PAS method and photographed with a photomicroscope. The arrows point at goblet cells and the stained area (reddish purple) indicates mucopolysaccharide. Mucopolysaccharide is also present in goblet cells.

As apparent from these Figures, goblet cells usually did not appear on the conjunctival epithelial surface of the normal rat which had been bred with a normal feed (see FIG. 4). However, goblet cells of the vitamin A deficient rat appeared on the conjunctival surface and the presence of mucopolysaccharide was confirmed in the cytoplasm (see FIG. 5). When a test drug was applied to rats in this state for 20 days, the amount of mucopolysaccharide in the cytoplasm was decreased in the goblet cells in a physiological saline solution applied group (see FIG. 6) and, on the other hand, the amount of mucopolysaccharide in the cytoplasm was large in a 0.5% present compound A applied group. Thus, it was seen that the state before application was retained (see FIG. 7).

(3) Results of Observation of Inferior Fornix Conjunctivae Goblet Cells with Scanning Electron Microscope The results of observation of inferior fornix conjunctivae goblet cells with a scanning electron microscope are shown in FIGS. 8 to 13.

Figure 8:
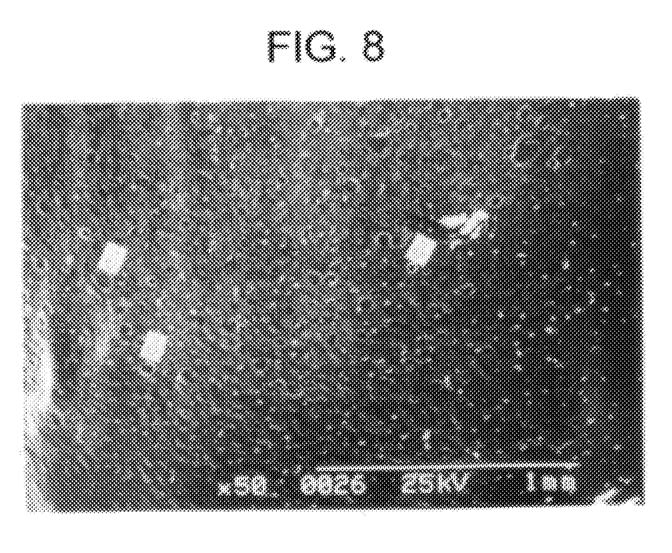
FIG. 8 is a scanning electron microscopic photograph of nasal inferior fornix conjunctivae cells of a normal rat. The cells were photographed using a scanning electron microscope in accordance with Test Example, experimental procedure (3) below.

FIG. 8 is a scanning electron microscopic photograph of the nasal inferior fornix conjunctivae from the eye of a normal rat. The photograph was taken using a scanning electron microscope. A white arrow indicates the opening of goblet cells.

Figure 9:
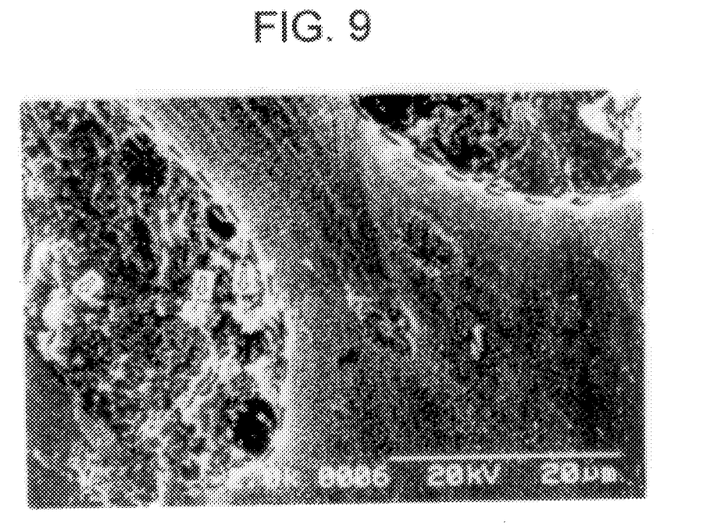
FIG. 9 is a scanning electron microscopic photograph of nasal inferior fornix conjunctivae cells of a normal rat. The cells were photographed using a scanning electron microscope in accordance with Test Example, experimental procedure (3) below, and represent an enlarged photograph of FIG. 8.

FIG. 9 is a scanning electron microscopic photograph of the nasal inferior fornix conjunctivae from the eye of a normal rat. The photograph was taken using a scanning electron microscope, and represents an enlarged photograph of FIG. 8. An opening of goblet cells is shown within the dashed line and mucopolysaccharide is observed (white arrows). Microvilli are recognized in a section separate from the openings of goblet cells.

Figure 10:
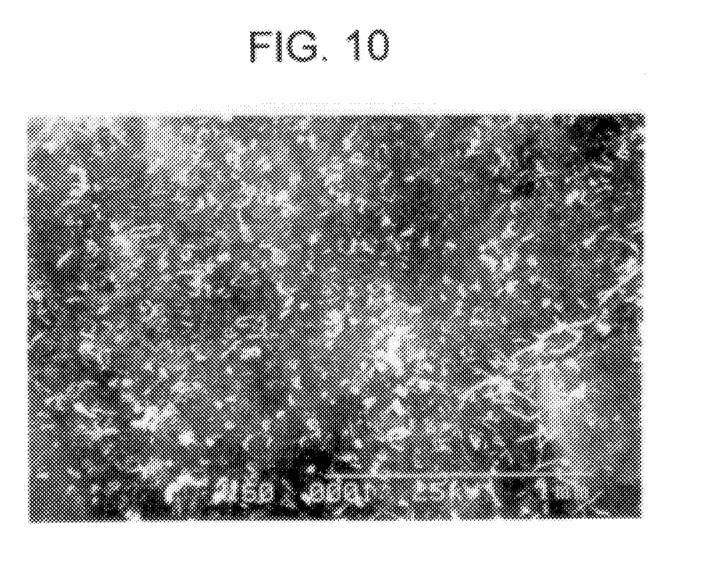
FIG. 10 is a scanning electron microscopic photograph of nasal inferior fornix conjunctivae cells of a vitamin A deficient rat which had received a physiological saline solution 8 times per day for 20 days. The cells were photographed using a scanning electron microscope in accordance with Test Example, experimental procedure (3) below.

FIG. 10 is a scanning electron microscopic photograph of nasal inferior fornix conjunctivae from the eye of a vitamin A deficient rat which had received application of a physiological saline solution 8 times per day for 20 days. The photograph was taken using a scanning electron microscope. No openings of goblet cells are recognized and an area where conjunctival epithelium are desquamated is observed.

Figure 11:
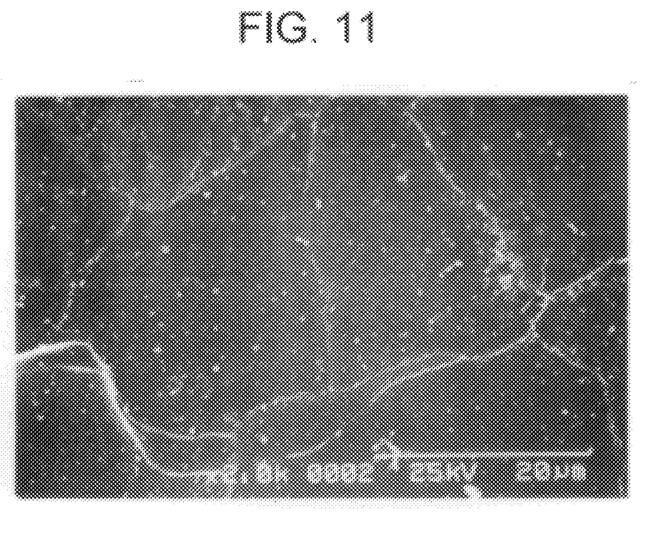
FIG. 11 is a scanning electron microscopic photograph of nasal inferior fornix conjunctivae cells of a vitamin A deficient rat which had received a physiological saline solution 8 times per day for 20 days. The cells were photographed using a scanning electron microscope in accordance with Test Example, experimental procedure (3) below, and represent an enlarged photograph of FIG. 10.

FIG. 11 is a scanning electron microscopic photograph of the nasal inferior fornix conjunctivae from the eye of a vitamin A deficient rat which had received application of a physiological saline solution 8 times per day for 20 days. The photograph was taken using a scanning electron microscope, and represents an enlarged photograph of FIG. 10. No openings of goblet cells are recognized and no microvilli are observed.

Figure 12:
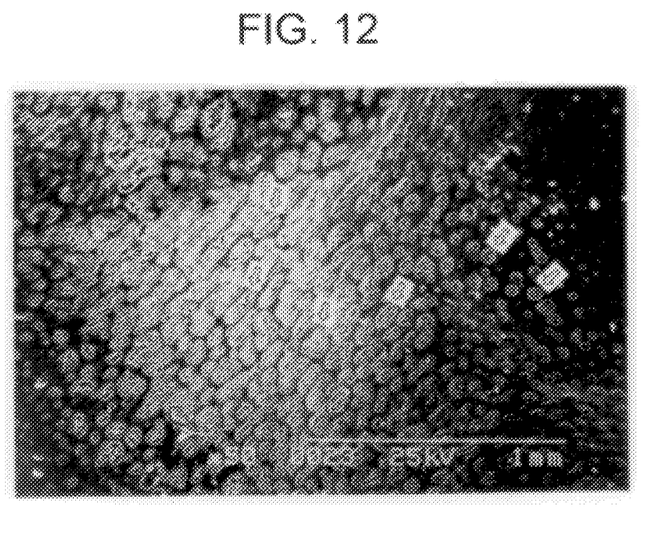
FIG. 12 is a scanning electron microscopic photograph of nasal inferior fornix conjunctivae cells of a vitamin A deficient rat which had received a 0.5% present compound A eyedrops 8 times per day for 20 days. The cells were photographed using a scanning electron microscope in accordance with Test Example, experimental procedure (3) below.

FIG. 12 is a scanning electron microscopic photograph of the nasal inferior fornix conjunctivae from the eye of a hypovitaminosis A rat which had received application of a 0.5% present compound A eye drop 8 times per day for 20 days. The photograph was taken using a scanning electron microscope. A white arrow indicates the opening of goblet cells. Goblet cells are opened more widely as compared with the normal state.

Figure 13:
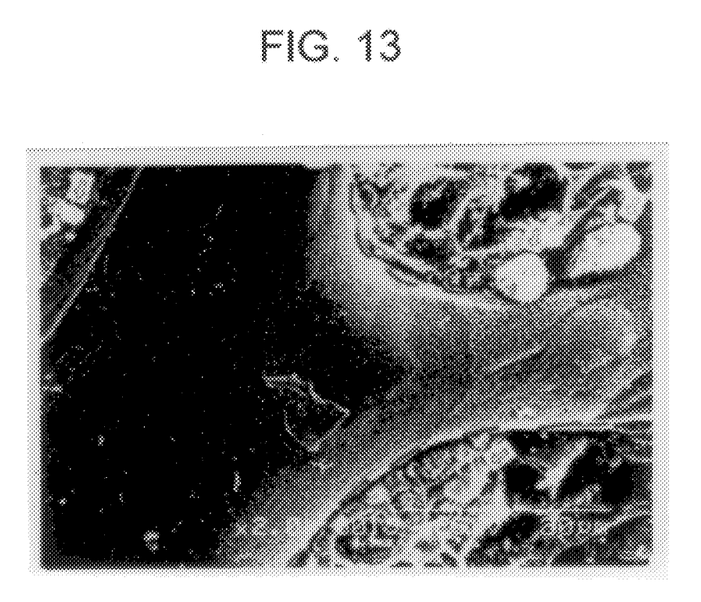
FIG. 13 is a scanning electron microscopic photograph of nasal inferior fornix conjunctivae cells of a vitamin A deficient rat which had received a 0.5% present compound A eyedrops 8 times per day for 20 days. The cells were photographed using a scanning electron microscope in accordance with Test Example, experimental procedure (3) below, and represent an enlarged photograph of FIG. 12.

FIG. 13 is a scanning electron microscopic photograph of the nasal inferior fornix conjunctivae from the eye of a vitamin A deficient rat which had received application of a 0.5% present compound A eye drop 8 times per day for 20 days. The photograph was taken using a scanning electron microscope, and represents an enlarged photograph of FIG. 12. The openings of goblet cells are shown within the dashed line and mucopolysaccharide (white arrows) is observed. Microvilli are observed in a section separate from the openings of goblet cells.

As apparent from FIGS. 8 and 9, in a normal rat, goblet cells were observed to be thinly opened in inferior fornix conjunctivae and mucin was present (see FIGS. 8 and 9). However, in a physiological saline solution applied group which had been bred with a vitamin A deficient feed, no openings of goblet cells were observed (see FIG. 10) and desquamation of epithelial cells and disappearance of microvilli were recognized (FIG. 11). On the other hand, on the surface of inferior fornix conjunctivae in a 0.5% present compound A applied group, many widely opened goblet cells were observed and mucopolysaccharide was present (see FIG. 12). Further, disappearance of epithelial cells was not observed (see FIG. 13).

Discussion on Test Results

As described above, the activity of the present compound A in delaying the progress of keratinizing keratoconjunctival lesion was studied using a vitamin A deficient rat having the symptom of keratinizing keratoconjunctival lesion which was established from the hypofunction of goblet cells and, as a result, it was made clear that a 0.5% present compound A applied group inhibits the progress of corneal keratinized disorder. Further, in histological observation of conjunctiva, more openings of goblet cells were recognized in a 0.5% present compound A applied group than in the normal state. And a 0.5% present compound A applied group was more similar to a normal state in respects of morphology of epithelial cells, the presence or absence of mucopolysaccharide in the cytoplasm and the like in comparison with a physiological saline solution applied group.

From these findings, it is presumed that the present compound functions on goblet cells by promoting the production of mucopolysaccharide. It is considered that, as a result of the activity, the morphology of epithelial cells is retained (microvilli are present) and the progress of corneal keratinized lesion is delayed. Therefore, it has been made clear that the present compound promotes the mucopolysaccharide producing function of goblet cells of a vitamin A deficient rat and, as a result, delays the progress of corneal keratinized lesion. Therefore, it is suggested that the present compound is a useful agent for preventing or treating dry eye or a disease caused therefrom.

What is claimed is:

1. A method for preventing or treating dry eye or a disease caused therefrom which comprises: applying to an eye of a patient a pharmaceutical composition comprising as an active ingredient an effective amount of a compound represented by the formula (I):

or a pharmacologically acceptable salt thereof; and a pharmaceutically acceptable carrier.

2. The method according to claim 1, wherein said dry eye is selected from the group consisting of hypolacrimation, tear deficiency, xerophthalmia, Sjögren's syndrome, keratoconjunctivitis sicca, Stevens-Johnson syndrome, ocular pemphigoid, blepharitis marginal, lid-closure failure and sensory nerve paralysis.

3. The method according to claim 1, wherein said dry eye is selected from the group consisting of allergic conjunctivitis-associated dry eye, post-viral conjunctivitis dry eye, post-cataract surgery dry eye, VDT operation-associated dry eye and contact lens wearing-associated dry eye.

4. The method according to claim 1, wherein said disease caused therefrom is selected from the group consisting of keratoconjunctival epithelial lesion, corneal epithelial erosion, corneal ulcer and ocular infectious disease.

* * * * *